United States Patent
Hong et al.

(10) Patent No.: US 11,667,916 B2
(45) Date of Patent: Jun. 6, 2023

(54) COMPOSITION FOR PREVENTING OR TREATING LIVER FIBROSIS, CONTAINING EXOSOME OR EXOSOME-DERIVED RIBONUCLEIC ACID

(71) Applicant: Korea University Research and Business Foundation, Seoul (KR)

(72) Inventors: Jae Sang Hong, Seoul (KR); Do Hoon Lee, Seoul (KR); Yu Jin Jang, Seoul (KR); Jong Hoon Kim, Seoul (KR); Young Sik Lee, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 491 days.

(21) Appl. No.: 16/645,180

(22) PCT Filed: Sep. 8, 2017

(86) PCT No.: PCT/KR2017/009910
§ 371 (c)(1),
(2) Date: Mar. 6, 2020

(87) PCT Pub. No.: WO2019/050071
PCT Pub. Date: Mar. 14, 2019

(65) Prior Publication Data
US 2020/0283763 A1 Sep. 10, 2020

(51) Int. Cl.
*C07H 21/02* (2006.01)
*C07H 21/04* (2006.01)
*C12N 15/113* (2010.01)
*A61P 1/16* (2006.01)
*A61K 35/28* (2015.01)
*A61K 35/407* (2015.01)

(52) U.S. Cl.
CPC ............ *C12N 15/113* (2013.01); *A61K 35/28* (2013.01); *A61K 35/407* (2013.01); *A61P 1/16* (2018.01); *C12N 2310/141* (2013.01)

(58) Field of Classification Search
CPC ................. C12N 15/113; C12N 2310/141
See application file for complete search history.

(56) References Cited

U.S. PATENT DOCUMENTS

2017/0298352 A1* 10/2017 Brigstock ............ C12Q 1/6883
2019/0350923 A1* 11/2019 Thum ................... A61P 21/00

FOREIGN PATENT DOCUMENTS

| KR | 10-2017-0103697 A | 9/2017 |
| WO | WO 2009/106367 A1 | 9/2009 |
| WO | WO 2016/054094 A1 | 4/2016 |
| WO | WO 2017/058938 A1 | 4/2017 |

OTHER PUBLICATIONS

International Search Report dated May 23, 2018 in corresponding International Patent Application No. PCT/KR2017/009910 (3 pages in English, 3 pages in Korean).
Hong et al., "Exosomes derived from mesenchymal stem cells and differentiated hepatocyte-like cells relieve liver fibrosis," International conference of The Korean Society for Molecular and Cellular Biology Sep. 21-23, 2015, COEX Center, Seoul, Republic of Korea, 2 pages.
Murakami et al., "The Progression of Liver Fibrosis is Related with Overexpression of the miR-199 and 200 Families," PLos ONE, Jan. 2011, vol. 6, Issue 1, 9 pages.
Li et al., "Exosomes Derived from Human Umbilical Cord Mesenchymal Stem Cells Alleviate Liver Fibrosis," Stem Celss and Development, vol. 22, No. 6, 2013, pp. 845-854.
Valencic et al., "Inhibition of mesenchymal stromal cells by pre-activated lymphocytes and their culture media," Stem Cell Research & Therapy, 2014, 9 pages.

* cited by examiner

*Primary Examiner* — Amy H Bowman
(74) *Attorney, Agent, or Firm* — NSIP Law

(57) ABSTRACT

The present invention relates to a composition or cell therapeutic agent for preventing or treating liver fibrosis, containing an exosome or exosome-derived ribonucleic acid. The exosome or ribonucleic acid derived therefrom, of the present invention, has effects of inhibiting activities of hepatic stellate cells and Kupffer cells and reducing the expression of α-SMA and inhibits the progression of liver fibrosis by inhibiting the deposition of collagen, thereby being effectively usable as a cell therapeutic agent for the prevention or treatment of liver fibrosis.

10 Claims, 24 Drawing Sheets
Specification includes a Sequence Listing.

[Fig 1]
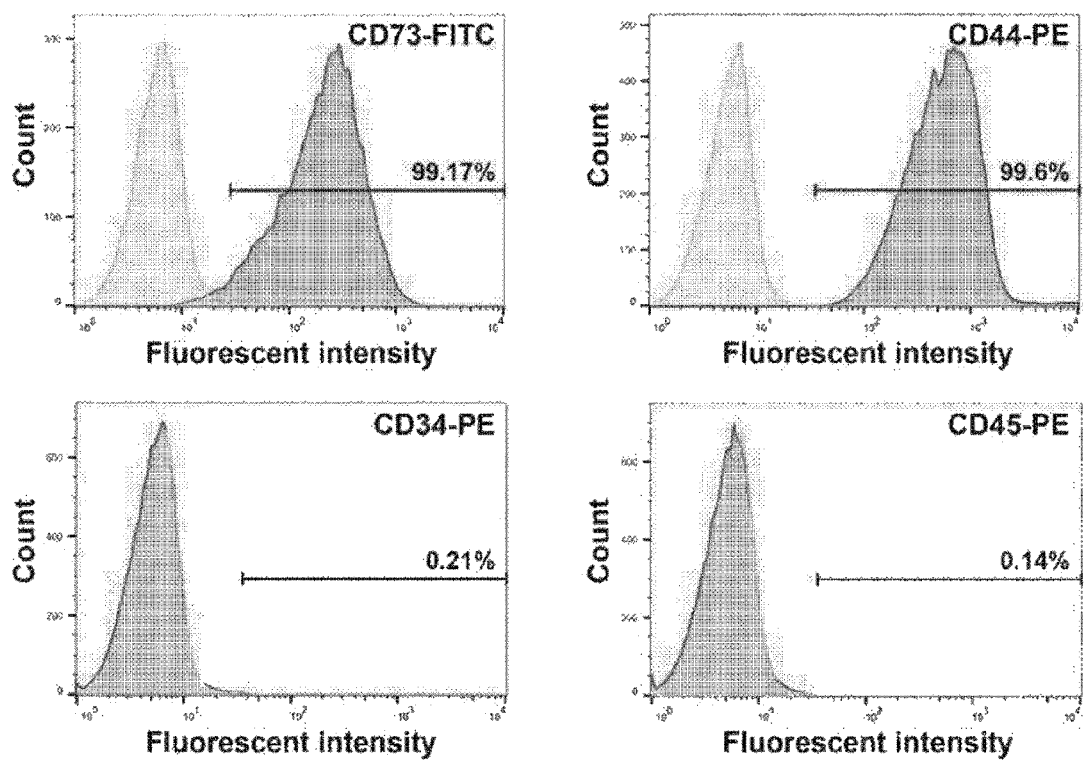

[Fig 2]
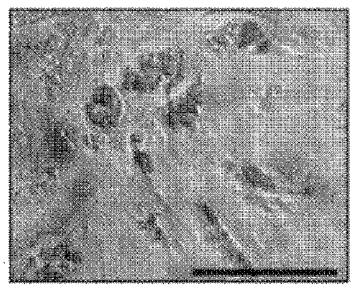 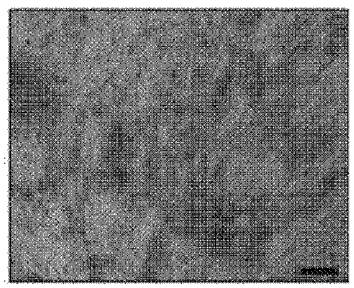 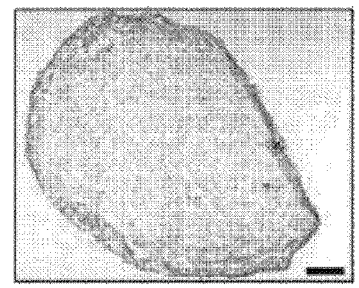

[Fig 3]
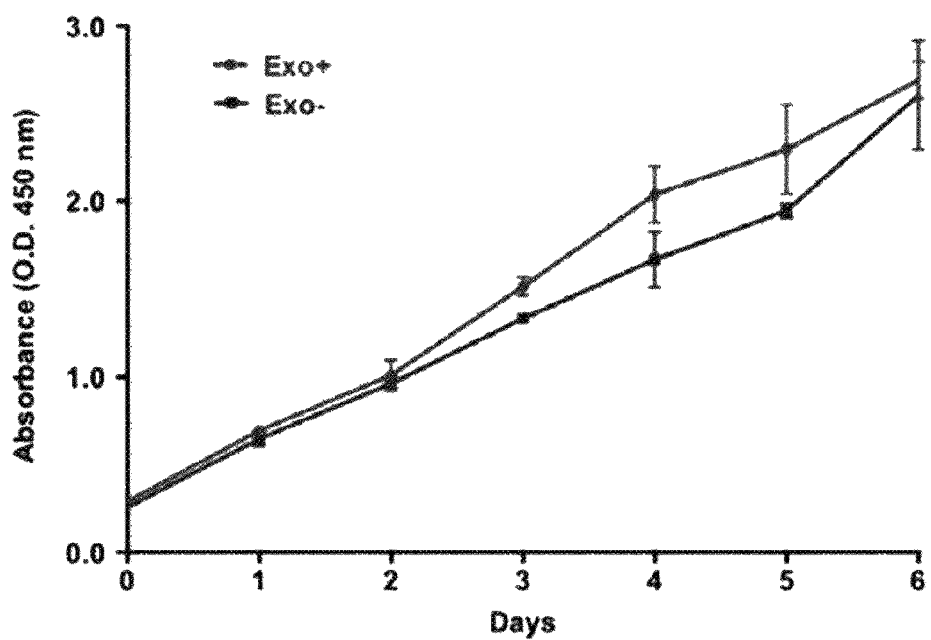

[Fig 4]

Step 1  $3.0 \times 10^3$ cell/cm² in coated 5 ng/cm² of collagen type I

↓ 80% confluence

Step 2  IMDM
+
20 ng/ml EGF, 10 ng/ml bFGF

↓ 48hr

Step 3  IMDM
+
20 ng/ml HGF, 10 ng/ml bFGF
0.61 mg/ml nicotinamide, 1% ITS

↓ 10 days

Step 4  IMDM
+
20 ng/ml oncostatin M, 1 uM dexamethasone, 1% ITS

↓ 10 days >

For each step medium was changed every 2 days

[Fig 5]
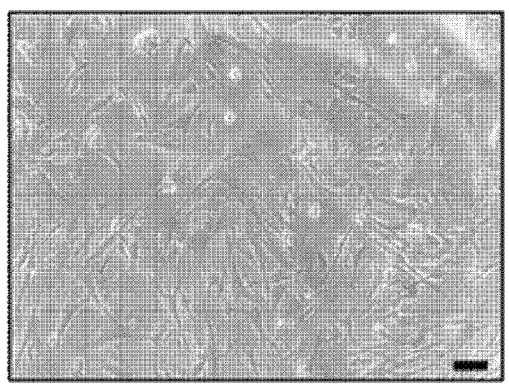
Step 1
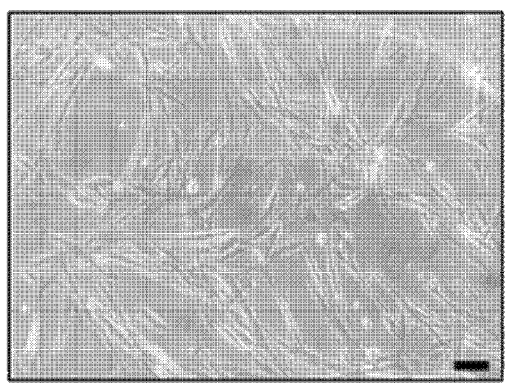
Step 2
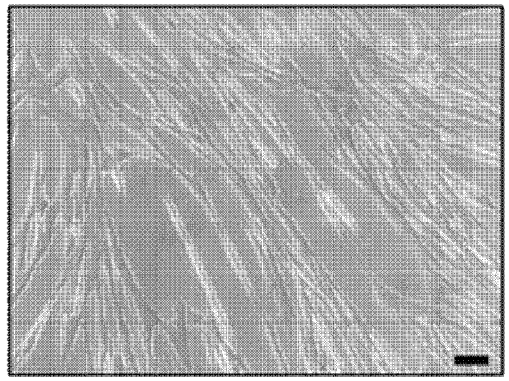
Step 3
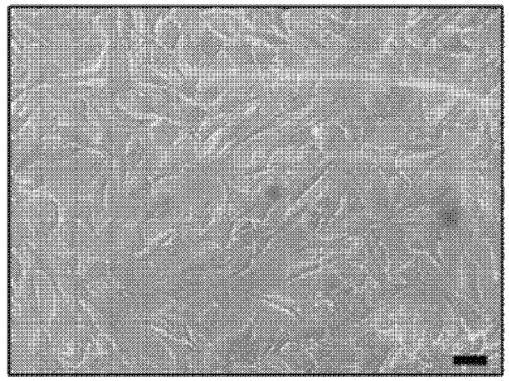
Step 4

[Fig 6]
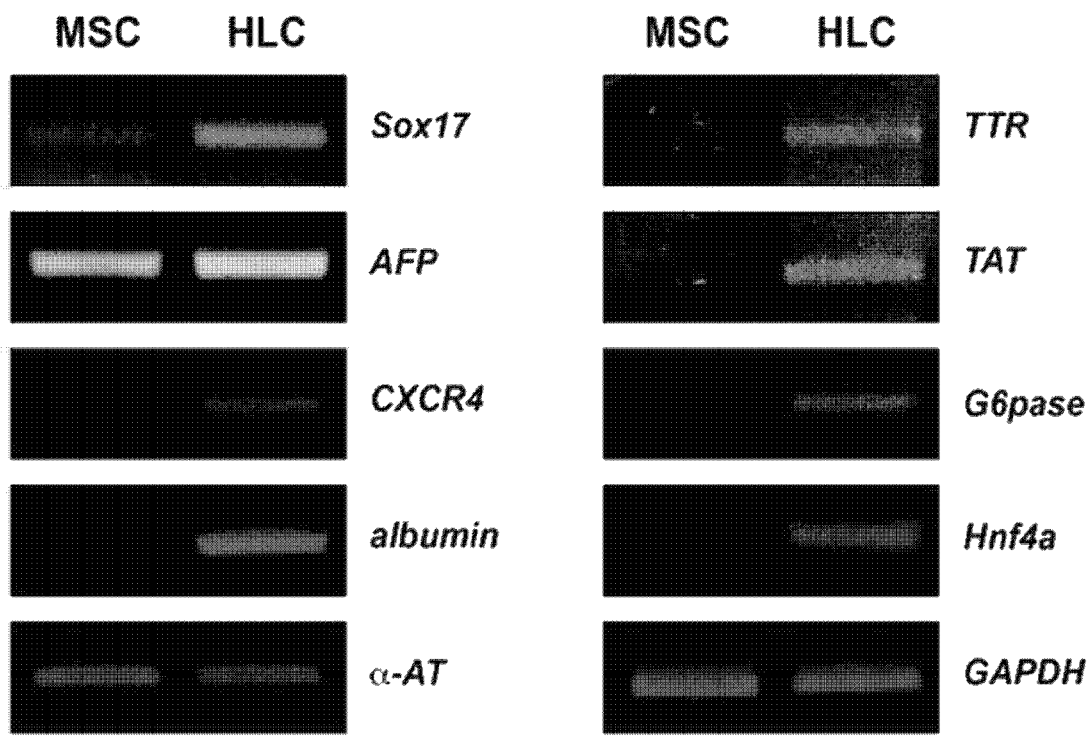

[Fig 7]
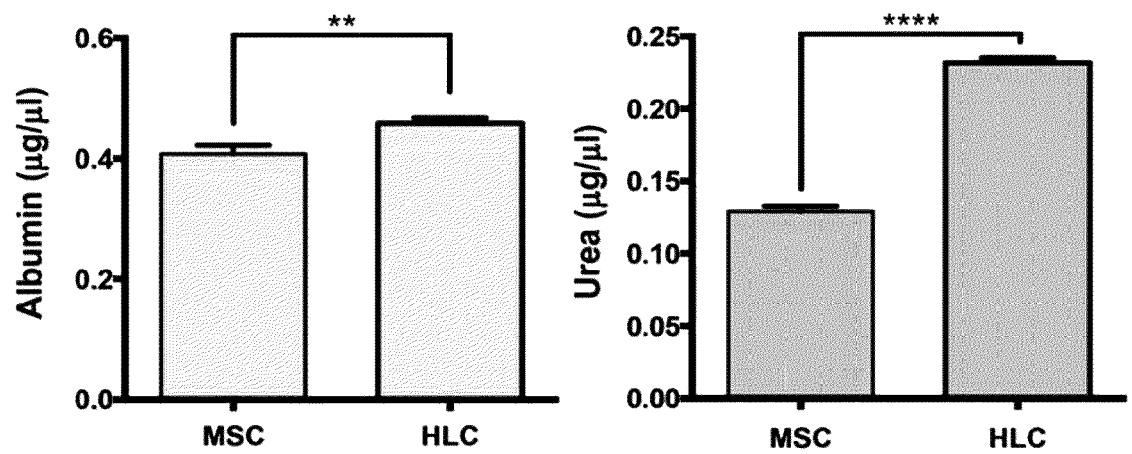

[Fig 8]
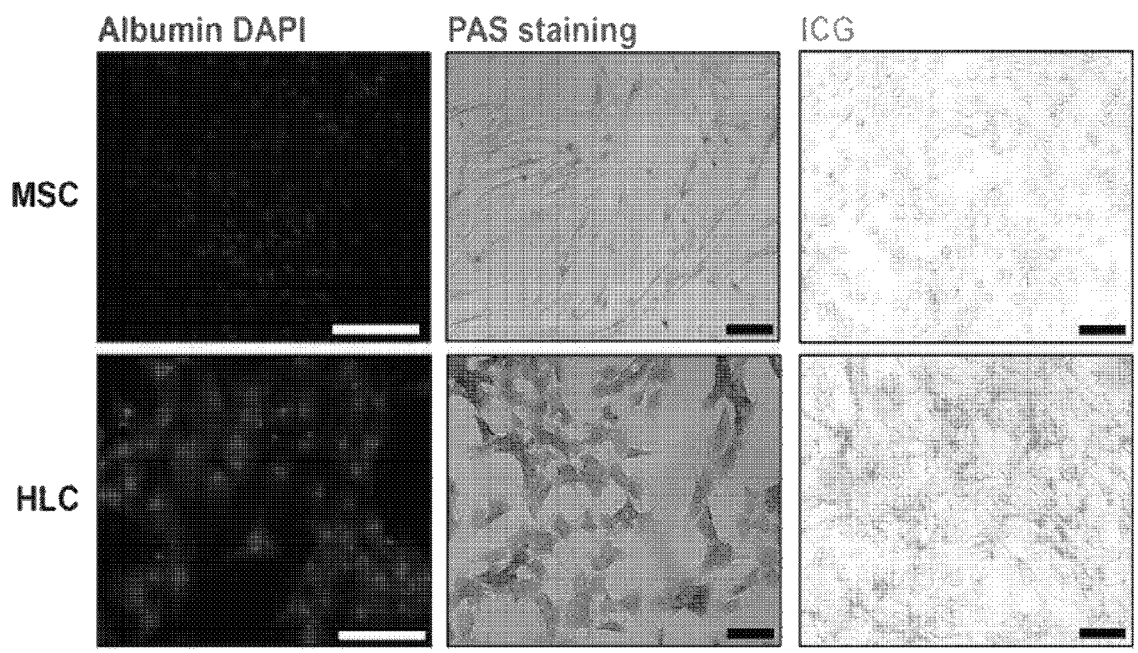

[Fig 9]

Culture the hucMSC or HLC at about 80% confluence for 48 hour
↓
Collect the culture medium
↓
Spindown the culture medium to remove cell debris
↓
Filtration (0.22 μm)
↓
Spindown the collected medium in centrifugal filter (100 MWCO)
↓
Add and mix the collected supernatant with ExoQuick-TC
↓
Incubate the mixture at 4°C for at least 12 hr
↓
Spindown the aggregates 1,500 g for 30 minute
↓
Remove supernatant
↓
Dissolve the pellet

[Fig 10]
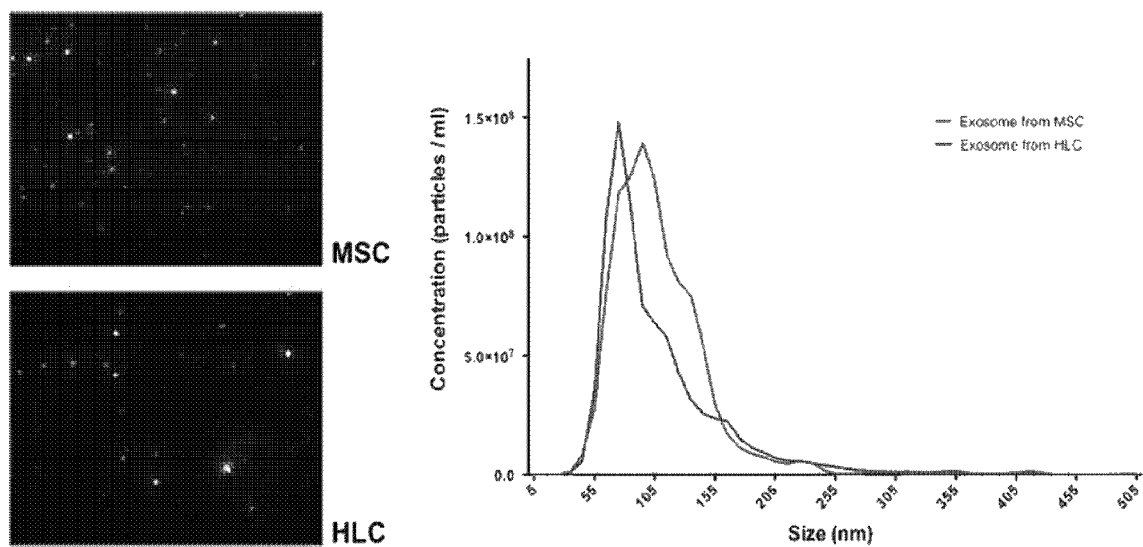

[Fig 11]
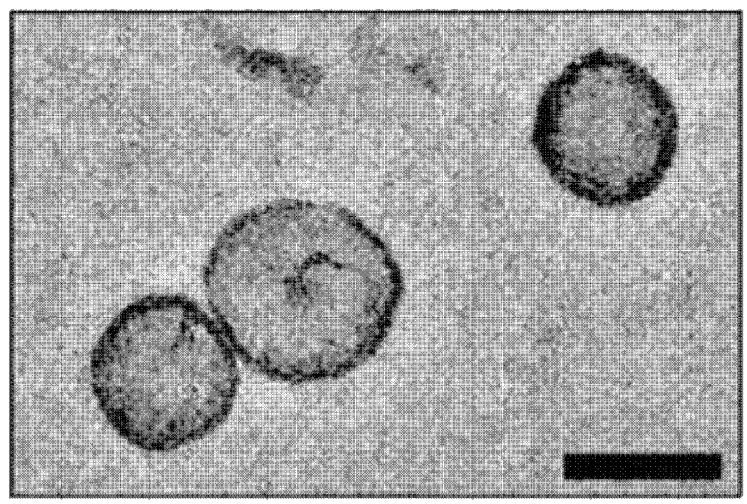
MSC
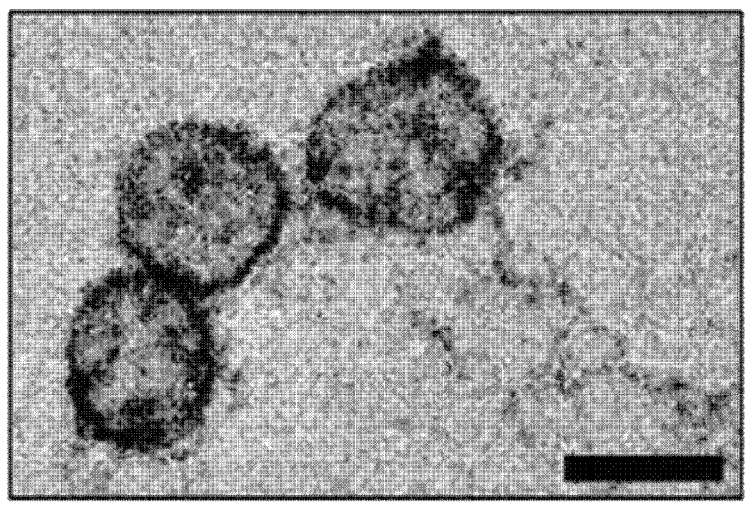
HLC

[Fig 12]
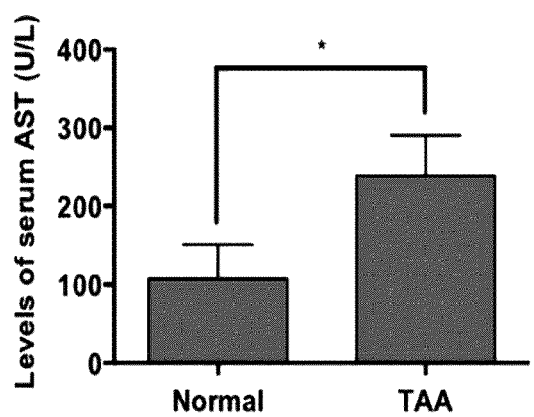 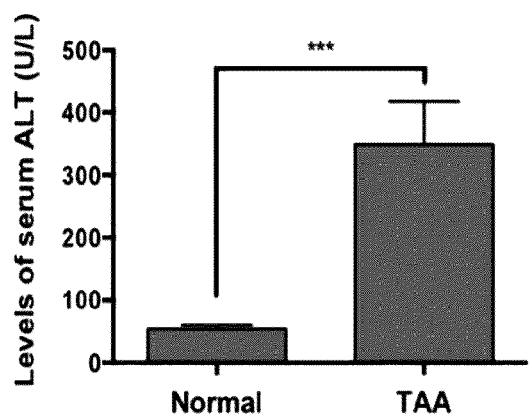

[Fig 13]
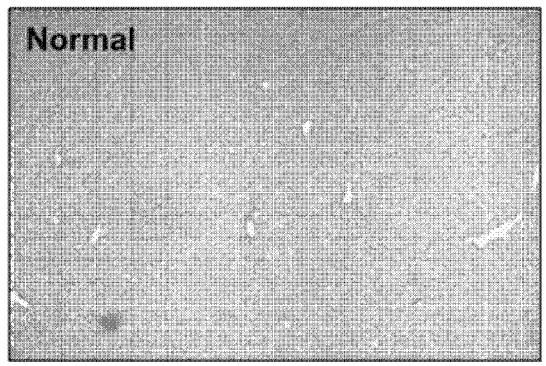 

[Fig 14]
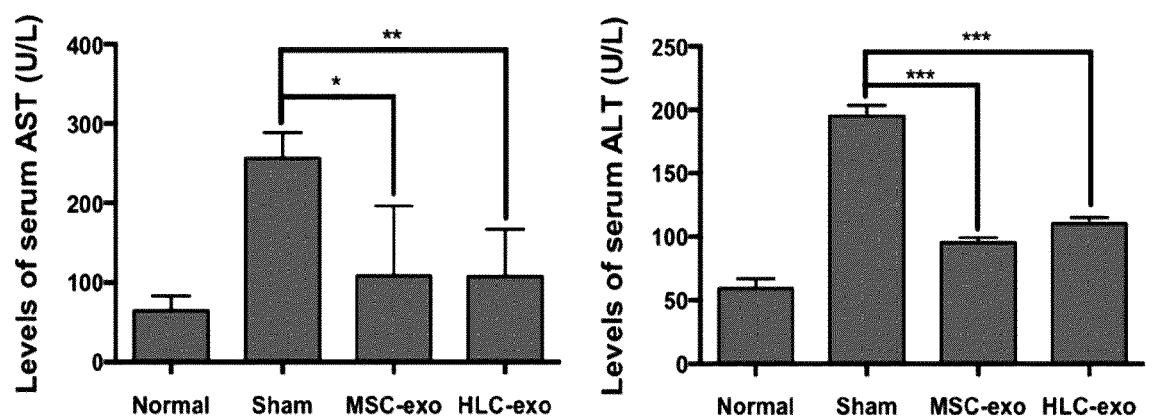

[Fig 15]
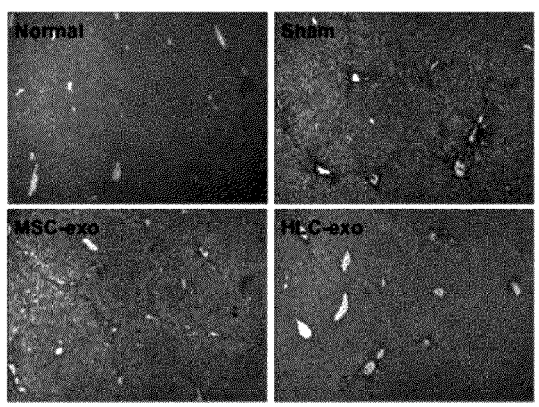
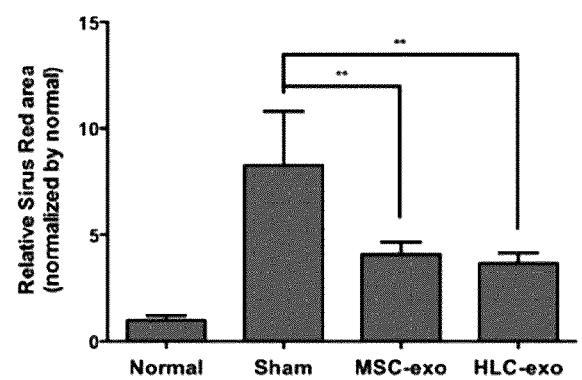

[Fig 16]
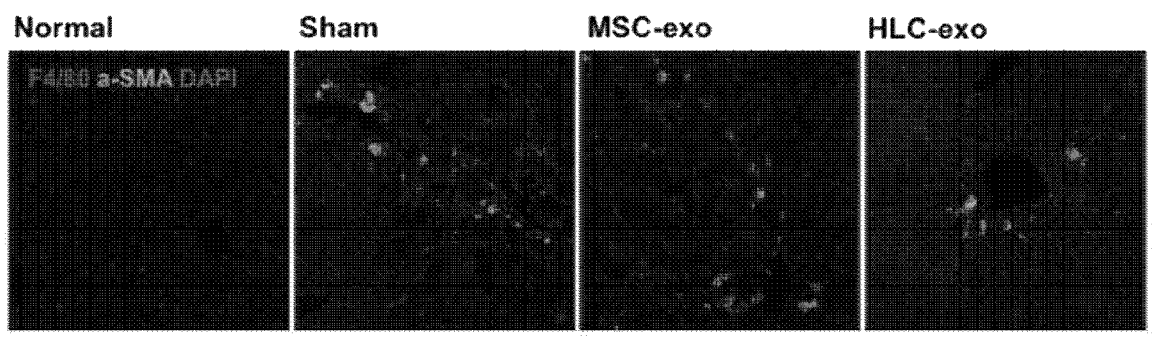

[Fig 17]
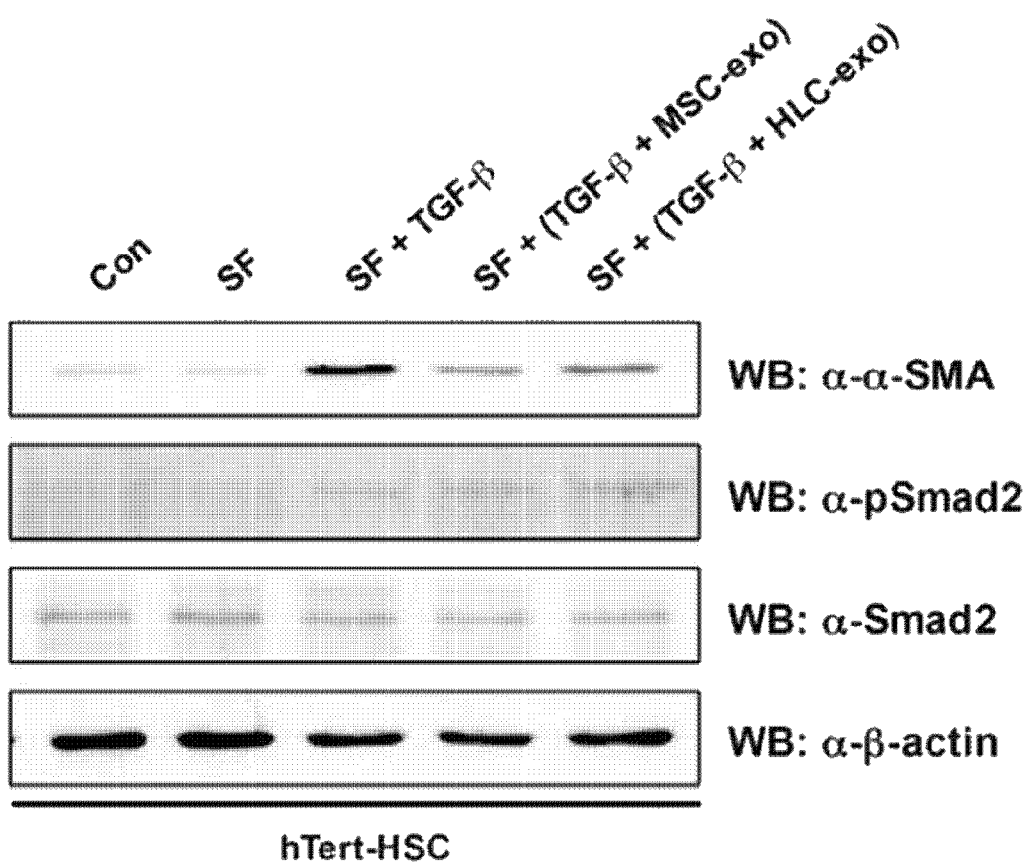

[Fig 18]
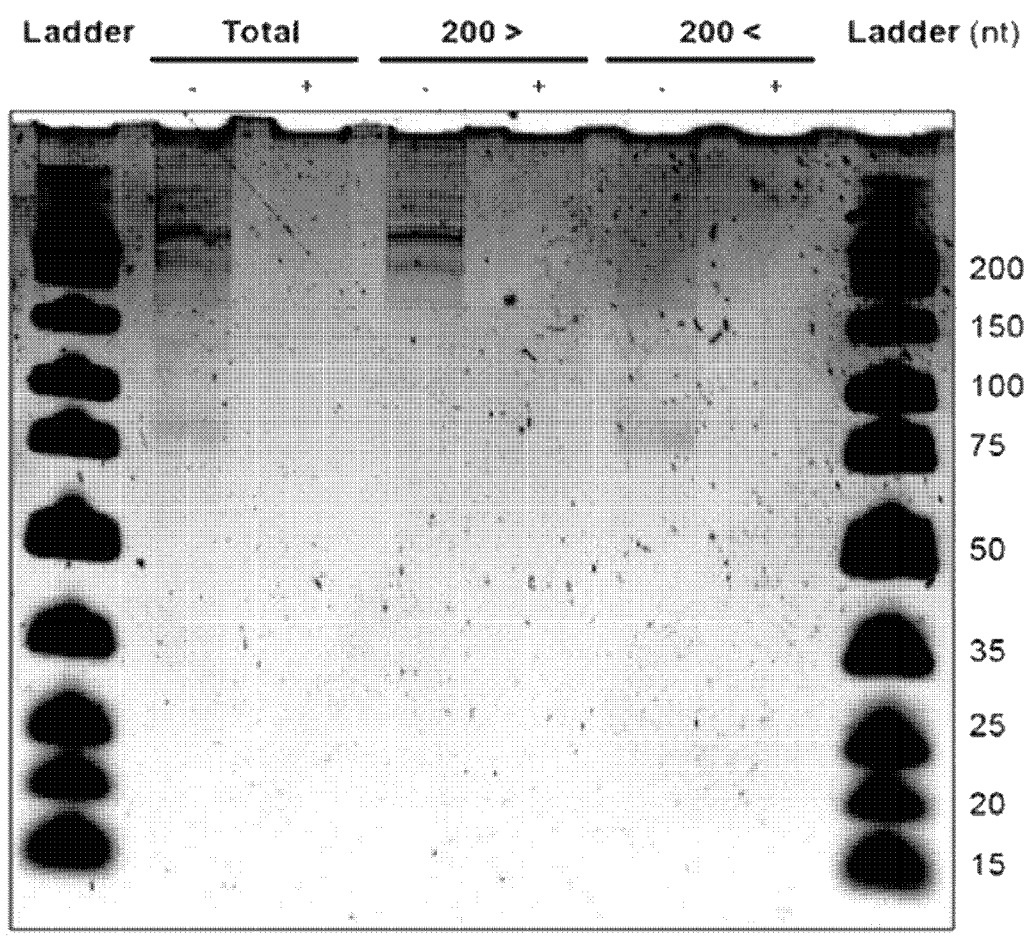

[Fig 19]
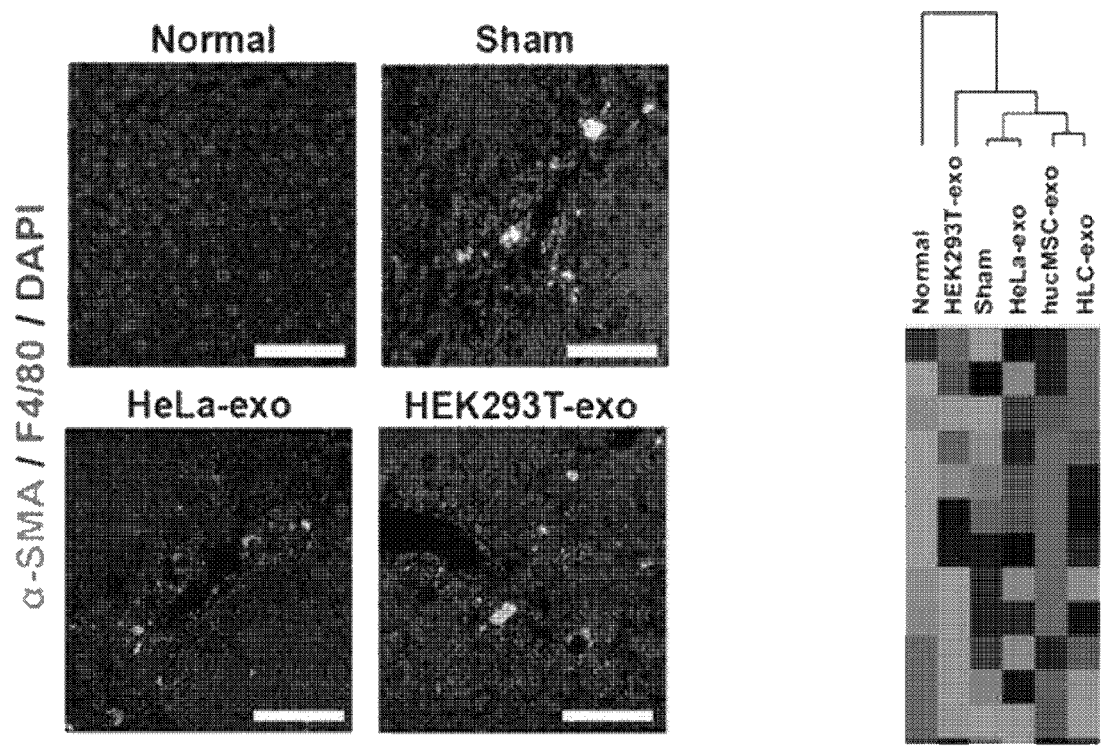

[Fig 20]
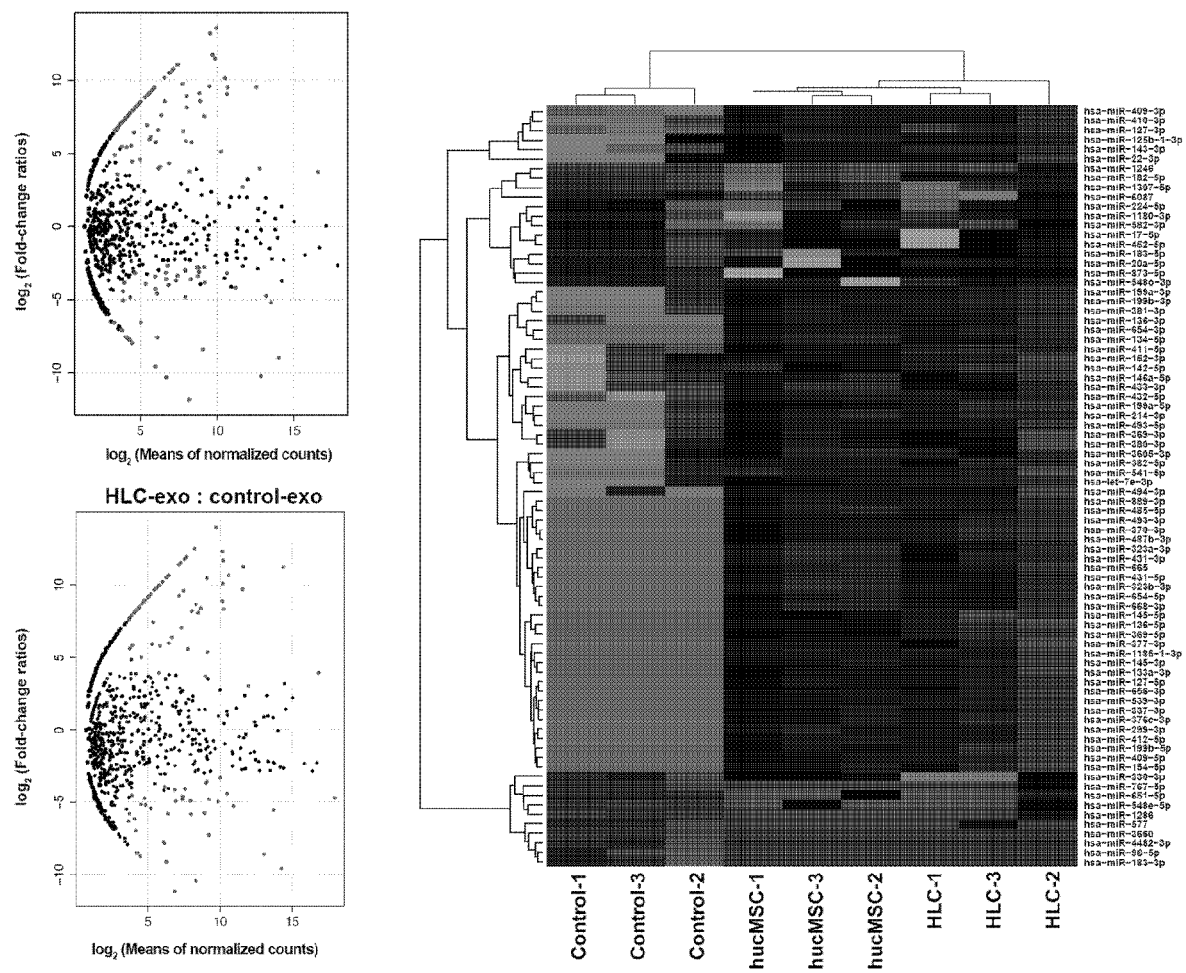

[Fig 21]
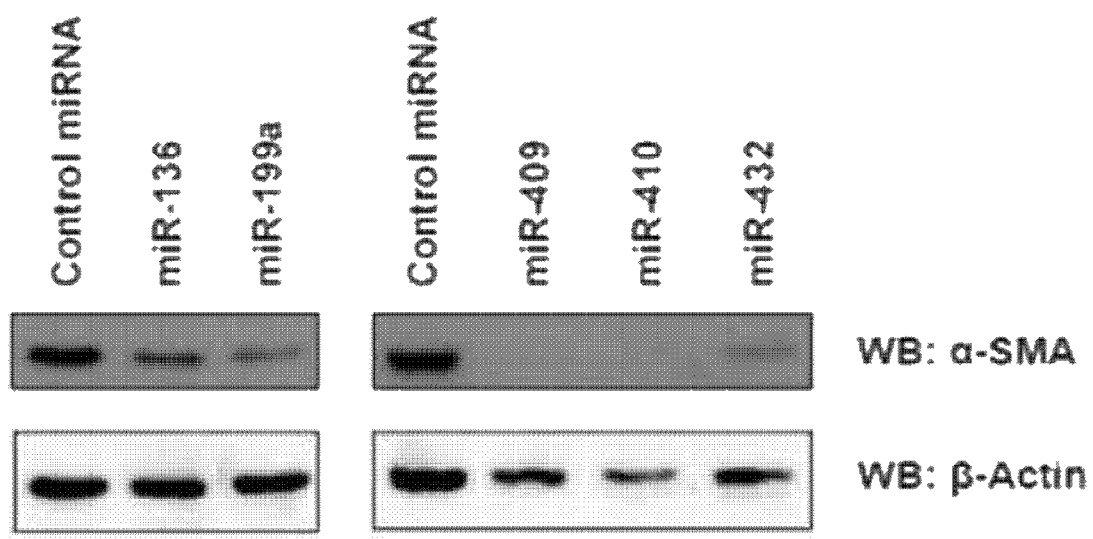

[Fig 22]
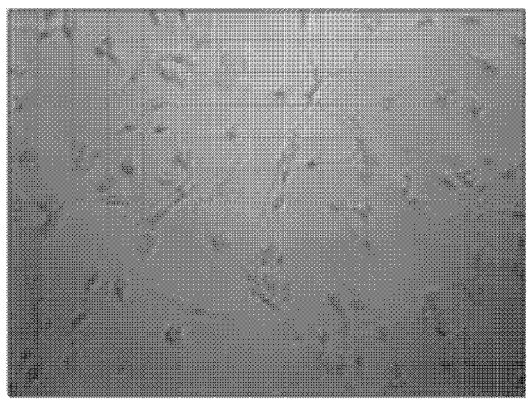
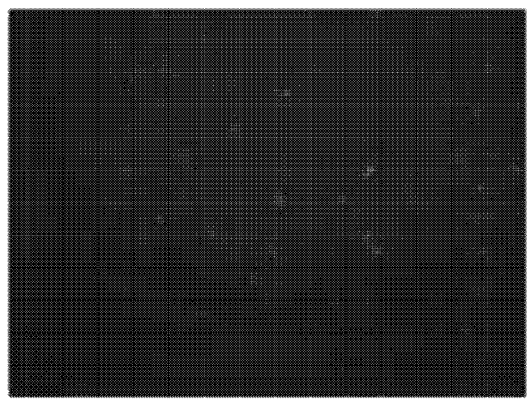
FLAG-Lamp2b exosome
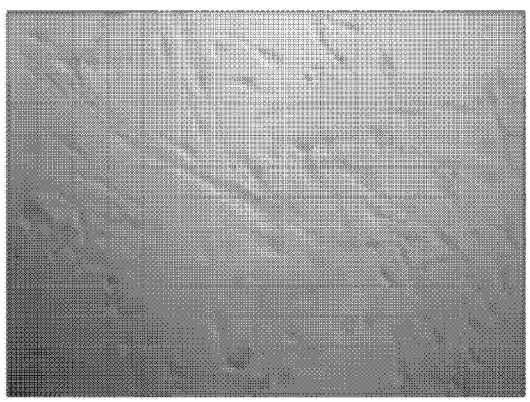
Peptide-Lamp2b exosome

[Fig 23]
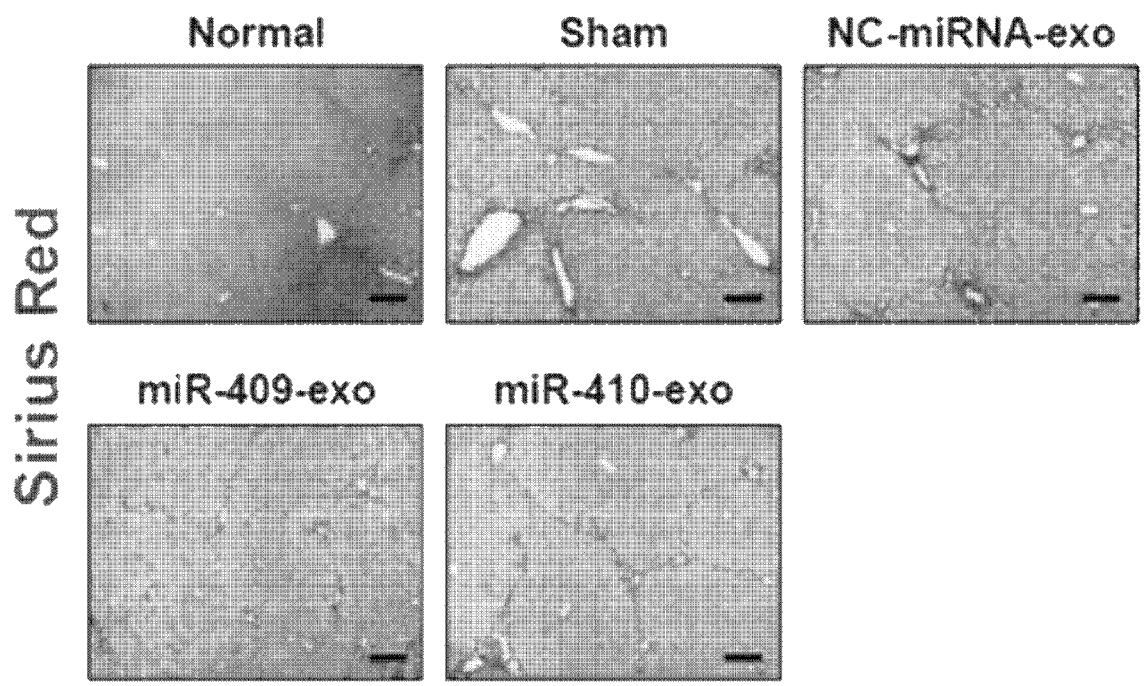

[Fig 24]
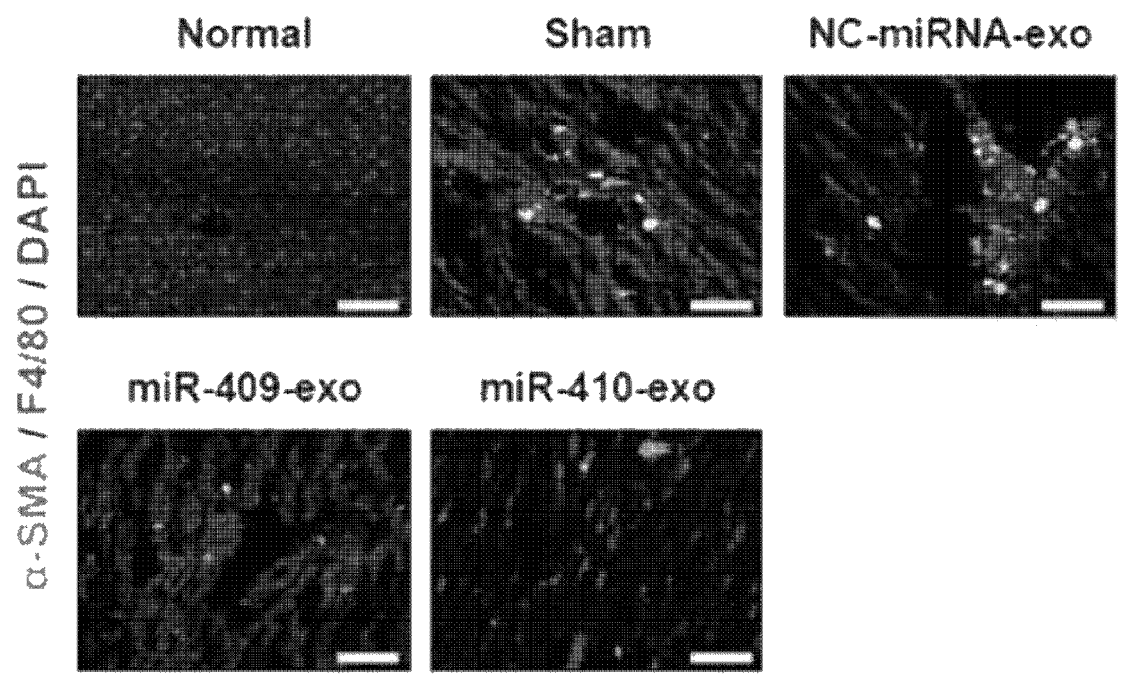

SEQUENCE LISTING

```
<160> NUMBER OF SEQ ID NOS: 5

<210> SEQ ID NO 1
<211> LENGTH: 22
<212> TYPE: RNA
<213> ORGANISM: Artificial Sequence
<220> FEATURE:
<223> OTHER INFORMATION: miR-136

<400> SEQUENCE: 1
caucaucguc ucaaaugagu cu                                              22

<210> SEQ ID NO 2
<211> LENGTH: 22
<212> TYPE: RNA
<213> ORGANISM: Artificial Sequence
<220> FEATURE:
<223> OTHER INFORMATION: miR-199a

<400> SEQUENCE: 2
acaguagucu gcacauuggu ua                                              22

<210> SEQ ID NO 3
<211> LENGTH: 22
<212> TYPE: RNA
<213> ORGANISM: Artificial Sequence
<220> FEATURE:
<223> OTHER INFORMATION: miR-409

<400> SEQUENCE: 3
gaauguugcu cggugaaccc cu                                              22

<210> SEQ ID NO 4
<211> LENGTH: 21
<212> TYPE: RNA
<213> ORGANISM: Artificial Sequence
<220> FEATURE:
<223> OTHER INFORMATION: miR-410

<400> SEQUENCE: 4
agguugucug ugaugaguuc g                                               21

<210> SEQ ID NO 5
<211> LENGTH: 23
<212> TYPE: RNA
<213> ORGANISM: Artificial Sequence
<220> FEATURE:
<223> OTHER INFORMATION: miR-432

<400> SEQUENCE: 5
ucuuggagua ggucauuggg ugg                                             23
```

COMPOSITION FOR PREVENTING OR TREATING LIVER FIBROSIS, CONTAINING EXOSOME OR EXOSOME-DERIVED RIBONUCLEIC ACID

CROSS REFERENCE TO RELATED APPLICATIONS

This application is a U.S. National Stage Application of International Application No. PCT/KR2017/009910 filed on Sep. 8, 2017, in the Korean Intellectual Property Office, the entire disclosure of which is incorporated herein by reference for all purposes.

TECHNICAL FIELD

The present invention relates to a composition or cell therapeutic agent for preventing or treating liver fibrosis, containing an exosome or exosome-derived ribonucleic acid.

BACKGROUND ART

Liver fibrosis is a wound healing process that is caused by the combination of collagen which is secreted in large amount from active hepatic stellate cells as the inflammatory response goes on because of damage to liver tissue and the extracellular matrix (ECM). Such a continuous progression of liver fibrosis leads to liver cirrhosis having abnormal structures that the deposition of collagen occurs in liver tissue in large amount and regenerative nodules are surrounded by collagen.

A chronic liver disease currently does not have a specific drug for clear cure. Especially, since the chronic liver disease is irreversible in the development of liver cirrhosis, the studies on the treatment method for chronic liver disease are in a stalemate state. However, the studies have shown that liver fibrosis, which is a preliminary stage of liver cirrhosis, can be improved depending on treatment methods, thus the liver fibrosis is recognized as a reversible disease unlike liver cirrhosis.

Currently, removal of causes of hepatocellular damage, mitigation of inflammatory reactions in liver tissue, inhibition of liver fibrosis factor activity, inhibition of active hepatic stellate cell activity, degradation of ECM, etc. have known as methods of inhibiting liver fibrosis progression. However, a gene therapy and treatment using stem cells are little known.

A cell therapy agent is defined as 'a drug that is used for the purposes of treatment, diagnosis, and prevention through a series of actions that change the biological characteristics of cells with various methods such as multiplying or screening live autologous, allogenic, or xenogenic cells in vitro so as to restore the functions of cells and tissues'.

A cell therapy agent can be broadly classified into a somatic cell therapy agent and a stem cell therapy agent depending on the type and the degree of differentiation of cells used. Once again, the stem cell therapy agent can be broadly classified into an embryonic stem cell therapy agent and an adult stem cell therapy agent according to the source of obtaining the stem cell. Currently, the adult stem cell therapy agent is a field where industrialization is considerably progressed, accounting for 99% of the global market of stem cell therapy agent.

A mesenchymal stem cell that is one of adult stem cells is a pluripotent cell capable of differentiating into mesenchymal tissues such as bone, cartilage, muscle, and liver in certain culture conditions, and has advantages in that it can be easily separated and can be obtained in an sufficient quantity without differentiation even in normal medium conditions. In addition, it has a very high utility value in that it helps cells to settle in the allogenic cell therapy and prolongs the survival of transplanted cells.

Recently, in the field of tissue regeneration, the therapeutic effects of the near secretion (paracrine) of substances produced from the mesenchymal stem cells, as well as a cell replacement therapy using mesenchymal stem cells, have been reported. In fact, it is confirmed that the mesenchymal stem cells secrete various substances (secretome) inducing nerve, angiogenesis and anti-inflammatory responses. The studies have reported that the secretome can be used to alleviate diseases such as cancer or heart disorders. Thus, in the field of tissue therapy and regeneration, the possibility of the cell-free therapy using the secretome was suggested. However, there are little studies on liver fibrosis, currently. Also, there is a lack of research on specifically which components are included in the secretome showing the treatment effect, and also, it is very lacking in understanding which mechanisms and regulatory networks of the secretome affect the recovery of damaged tissue in a specific disease. Therefore, further researches are needed to complement this.

Meanwhile, exosome included in the secretome is an important medium for transporting specific components from one cell to another, which is known to cause gene expression changes in the cell that accepts it. It is confirmed that exosome is a particle having a size of 40 to 100 nm, acts as extracellular vesicles, and is secreted from various cells such as stem cells, and is present in blood, biological fluid, urine, and culture medium of cell.

These exosomes are produced through the fusion of late-endosome produced by an intracellular endosome trafficking pathway and plasma membranes.

Exosome includes not only certain proteins and mRNA transcriptomes that are expressed in the corresponding cells, but also, importantly, various small non-coding RNAs (microRNA, piRNA, etc.) that regulate the expression of genes as RNA itself. Therefore, it is known that exosomes reflect the genetic characteristics of the cells from which they originated.

Small non-coding RNAs (ncRNA) among the substances constituting exosomes can have various gene expression control effects even in very small amounts, and also have a great influence because a ncRNA can be involved in a wide variety of signaling pathways. A ncRNA is a type of RNA transcriptomes that is not translated into protein but is reported to control the stability, transcription and translation of various genes. 97% of RNAs transcribed from the human genome are ncRNAs that are not translated into proteins. Therefore, since ncRNA is closely related to various biological processes in vivo, the research on ncRNA is considered a hot issue in the field of life science.

In particular, among these ncRNAs, microRNAs are small RNAs having a size of about 22 nucleotides and induce RNA interference phenomena that regulate gene expression by degrading nucleotide sequence complementary mRNA or inhibiting translation into proteins. RNA interference is closely related to almost all biological processes, including the development and physiology of living organisms, the differentiation, proliferation and death of cells, and the stability of the genome, as well as the resistance to viruses and various human diseases. Competitive research for the development of therapeutic agents for human diseases based on the association between RNA interference and diseases is ongoing internationally.

Therefore, the economic market size using RNA interference technology continues to increase due to the infinite possibilities in the field of medical applications including the basic fields. According to Frost & Sullivan's research, the world market for RNA interference technology has grown tremendously from 48 million in 2003 to 328 million in 2010. In addition, the new report released by BBC Research estimated that the annual average growth rate will reach 83.4% in 2013, at 3.6 billion. In addition, Jain PharmaBioTech study showed that the development of new drugs based on RNA interference technology has doubled from 500 million in 2004 to 1 billion in 2010. Another survey predicted that the industrial market for RNA interference therapy would reach 2.3 billion in 2013.

Therefore, there is a need for a new treatment method that can make a major change in existing limited treatment by verifying the recovery of liver fibrosis by mesenchymal stem cell-derived exosomes based on these studies.

DISCLOSURE

Technical Problem

Accordingly, the present inventors have discovered exosomes and exosomal RNAs (Ribonucleic acids) that are effective in the recovery of liver fibrosis to study their inhibitory effect on liver fibrosis. As a result, the present invention has been accomplished by confirming that they have a possibility of being used as a therapeutic agent having economically excellent effect in the future.

Therefore, an object of the present invention is to provide a pharmaceutical composition for preventing or treating liver fibrosis, in which the composition includes an exosome or an exosomal RNA.

Another object of the present invention is to provide a food composition for preventing or improving liver fibrosis, in which the food composition includes an exosome or an exosomal RNA.

Yet another object of the present invention is to provide a cell therapy agent for preventing or treating liver fibrosis, in which the cell therapy agent includes an exosome or an exosomal RNA.

Still another object of the present invention is to provide a method for preventing or treating liver fibrosis, in which the method includes administering an exosome or an exosomal RNA to an individual in need thereof.

Still another object of the present invention is to provide a method for improving liver fibrosis, in which the method includes administering an exosome or an exosomal RNA to an individual in need thereof.

Technical Solution

In order to achieve the objects as described above, the present invention provides a pharmaceutical composition for preventing or treating liver fibrosis, in which the composition includes an exosome or an exosomal RNA.

Further, the present invention provides a food composition for preventing or improving liver fibrosis, in which the food composition includes an exosome or an exosomal RNA.

Further, the present invention provides a cell therapy agent for preventing or treating liver fibrosis, in which the cell therapy agent includes an exosome or an exosomal RNA.

Further, the present invention provides a method for preventing or treating liver fibrosis, in which the method includes administering an exosome or an exosomal RNA to an individual in need thereof.

Further, the present invention is to provide a method for improving liver fibrosis, in which the method includes administering an exosome or an exosomal RNA to an individual in need thereof.

Advantageous Effects

The exosome or ribonucleic acid derived therefrom, of the present invention, has effects of inhibiting the activities of hepatic stellate cells and Kupffer cells and reducing the expression of α-SMA and inhibits the progression of liver fibrosis by inhibiting the deposition of collagen, thereby being effectively usable as a cell therapeutic agent for the prevention or treatment of liver fibrosis.

DESCRIPTION OF DRAWINGS

FIG. 1 shows the analysis result of markers of mesenchymal stem cells.

FIG. 2 shows the results of inducing the differentiation of mesenchymal stem cells into fat, bone, and chondrocyte (scale bar: 100 μm).

FIG. 3 shows the results of confirming the proliferation of mesenchymal stem cells in a culture medium containing exosome deficient FBS.

FIG. 4 shows a step of inducing the differentiation from undifferentiated mesenchymal stem cells into hepatocyte-like cells.

FIG. 5 shows morphological changes according to a step of differentiation from undifferentiated mesenchymal stem cells to hepatocyte-like cells (scale bar: 100 μm).

FIG. 6 shows the analysis results of expression of hepatocyte-associated genes in mesenchymal stem cells and hepatocyte-like cells using RT-PCR.

FIG. 7 shows the analysis results of the secretion ability of albumin and urea in mesenchymal stem cells and hepatocyte-like cells.

FIG. 8 shows the analysis results of glycogen storage capacity and ICG absorption function in hepatocyte-like cells (scale bar: 100 μm).

FIG. 9 is a flowchart showing isolation of exosomes from undifferentiated mesenchymal stem cells and hepatocyte-like cells.

FIG. 10 is a diagram confirming the size distribution of exosomes isolated from undifferentiated mesenchymal stem cells and hepatocyte-like cells through NTA analysis.

FIG. 11 shows observation results of exosomes isolated from undifferentiated mesenchymal stem cells and hepatocyte-like cells by a transmission electron microscope (TEM) (scale bar: 100 nm).

FIG. 12 shows the results of a hepatic toxicity test for a chronic liver fibrosis animal model.

FIG. 13 shows the results of confirming the degree of collagen deposition in a chronic liver fibrosis animal model.

FIG. 14 shows the results of hepatic toxicity test by treatment with exosomes in mesenchymal stem cells and hepatocyte-like cells.

FIG. 15 shows the results of confirming the degree of collagen deposition by treatment with exosomes in mesenchymal stem cells and hepatocyte-like cells.

FIG. 16 shows the analysis results of the activities of hepatic stellate cells and Kupffer cells by treatment with exosomes in mesenchymal stem cells and hepatocyte-like cells.

FIG. 17 shows the analysis results of expression of α-SMA by treatment with exosomes in mesenchymal stem cells and hepatocyte-like cells.

FIG. 18 shows the results of isolating and confirming small RNAs present in exosomes isolated from mesenchymal stem cells and hepatocyte-like cells.

FIG. 19 shows the results of immunofluorescence staining and analysis of gene expression of liver tissue after administration of exosomes derived from HeLa cells and HEK293T cells.

FIG. 20 shows the analysis-comparison results of expression of exosomal microRNA derived from mesenchymal stem cells and hepatocyte-like cells.

FIG. 21 shows the analysis results of activity of hepatic stellate cells transfected with the microRNAs according to the present invention and the control.

FIG. 22 shows the results of confirming the effect of transferring the hepatic stellate cell targeting peptide-fused exosomal microRNA into the hepatic stellate cells.

FIG. 23 shows the results of Sirius Red staining of liver tissue after administration of microRNA to a liver fibrosis animal model.

FIG. 24 shows the results of immunofluorescence staining of liver tissue after administration of microRNA to a liver fibrosis animal model.

BEST MODE

Hereinafter, the present invention will be described in detail.

The present invention provides a composition for preventing or treating liver fibrosis, in which the composition comprises an exosome or an exosomal RNA.

The composition includes a pharmaceutical composition or a food composition.

The term "exosome" as used herein means a small vesicle having membrane structure that is secreted from various cells in which the diameter of the exosome is about 30 nm to about 100 nm, which refers to a small vesicle that is released into the extracellular environment by fusing polycystic structure with the plasma membrane.

In the present invention, the exosomes may be derived from mesenchymal stem cells or hepatocyte-like cells.

The term "stem cell" as used herein refers to a cell having the ability to self-replicate as an undifferentiated cell and the ability to differentiate into two or more different types of cells.

The stem cells may be autologous or allogeneic stem cells and may be derived from any type of animal including human and non-human mammals. The stem cells are not limited to those derived from an adult or those derived from an embryo.

The stem cells of the present invention include embryonic stem cells, adult stem cells, or dedifferentiated stem cells, and preferably, the stem cells are the adult stem cells. The adult stem cells can be isolated from various tissues and include, for example, placenta-derived stem cells, bone marrow-derived stem cells, cord blood-derived stem cells, fat-derived stem cells, stillborn fetal brain-derived neural stem cells, or mesenchymal stem cells derived from adult cells, and preferably human mesenchymal stem cells, but is not limited thereto. The mesenchymal stem cells may be, but are not limited to, mesenchymal stem cells derived from cord, umbilical cord blood, bone marrow, fat, muscle, nerve, skin, amniotic membrane, placenta, etc.

The hepatocyte-like cell (HLC) of the present invention includes cells in which the differentiation is induced from undifferentiated mesenchymal stem cells into hepatocyte. The method of inducing differentiation from undifferentiated mesenchymal stem cells is known in the art.

The term "exosomal RNAs" as used herein refer to RNAs derived from exosomes.

The term "RNAs" as used herein may include small RNAs. The term "small RNAs" as used herein refers to RNAs with a short length of 200 nucleotides or less in length which do not translate into proteins and effectively inhibit translation of specific mRNAs through complementary binding. Small RNAs include siRNAs (small interfering RNAs), miRNAs (microRNAs), piRNAs (Piwi-associated RNAs), Longer non-coding RNAs, etc.

siRNAs are formed by cleavage of long double-stranded RNA molecules (20 to 25 nucleotides in length). siRNAs are particularly important to counteract the active taming of the transposon and viral infections and may regulate the gene encoding the protein. The synthesized siRNA may be artificially expressed for experimental purposes.

miRNA (microRNA) is a small RNA that is encoded by a specific gene and is a single-stranded RNA molecule, which binds to the 3'-UTR of mRNA (messenger RNA) to control the expression of eukaryotic genes (20 to 25 nucleotides in length). miRNA is produced with a stem-loop structure precursor miRNA (pre-miRNA) by Drosha (RNase III type enzyme), and it is transferred to the cytoplasm and cleaved by Dicer to be made into mature miRNA. In the present invention, the number of miRNAs is the number assigned according to the order in which the small RNAs are discovered, which is obvious to those skilled in the art (http://www.mirbase.org).

piRNA is a small RNA generated from a long single-stranded precursor (25 to 30 nucleotides in length). piRNA functions in association with the piwi subfamily of the Argonaute protein and is essential for the development of germ cells.

The RNAs of the present invention are derived from exosomes and may affect liver fibrosis and may be, for example, miR-136, miR-199a, miR-409, miR-410 or miR-432, but is not limited thereto.

The composition of the present invention may include, but is not limited to, the miRNA itself, but may include fragments thereof.

More specifically, the miR-136 may be represented by SEQ. ID NO: 1 in which the nucleotide sequence is a mature form of miR-136 and is derived from precursor microRNA having a hairpin structure.

5'-CAUCAUCGUCUCAAAUGAGUCU (SEQ. ID NO: 1)-3'

More specifically, the miR-199a may be represented by SEQ. ID NO: 2 in which the nucleotide sequence is a mature form of miR-199a and is derived from precursor microRNA having a hairpin structure.

5'-ACAGUAGUCUGCACAUUGGUUA (SEQ. ID NO: 2)-3'

More specifically, the miR-409 may be represented by SEQ. ID NO: 3 in which the nucleotide sequence is a mature form of miR-409 and is derived from precursor microRNA having a hairpin structure.

5'-GAAUGUUGCUCGGUGAACCCCU (SEQ. ID NO: 3)-3'

More specifically, the miR-410 may be represented by SEQ. ID NO: 4 in which the nucleotide sequence is a mature form of miR-410 and is derived from precursor microRNA having a hairpin structure.

5'-AGGUUGUCUGUGAUGAGUUCG (SEQ. ID NO: 4)-3'

More specifically, the miR-432 may be represented by SEQ. ID NO: 5 in which the nucleotide sequence is a mature form of miR-432 and is derived from precursor microRNA having a hairpin structure.

5'-UCUUGGAGUAGGUCAUUGGGUGG (SEQ. ID NO: 5)-3'

The present invention also includes nucleic acid molecules having nucleotide sequences complementary to the nucleotide sequences represented by SEQ ID NOS: 1 to 5, respectively, and a variant capable of functionally performing the same function.

The nucleic acid molecule of the present invention may be nucleic acid analog molecules such as RNA, DNA, sugar- or backbone-modified nucleotides or deoxyribonucleotides. It may also be, but not limited to, other nucleic acid analog molecules such as PNA (peptide nucleic acids) or LNA (locked nucleic acids).

The nucleic acid molecule of the present invention may be adapted to efficiently and smoothly introduce into a cell. For example, the nucleic acid can be conjugated to and/or complexed with a delivery reactant (e. g., cationic liposome). In some cases, the nucleic acid may be complexed with, or conjugated to, a protein (e.g., Atelocollagen) that increases the nuclease resistance of the oligonucleotide and enhances cellular uptake.

The term "liver fibrosis" as used herein refers to a state of increased fiber in the liver due to the results of liver disorder.

In the present invention, liver fibrosis may include without limitation diseases that may be caused by an increase in liver fiber, and may include at least one selected from the group consisting of liver fibrosis, portal cirrhosis, necrotizing cirrhosis, biliary cirrhosis, nutritional cirrhosis, alcoholic cirrhosis, viral hepatitis cirrhosis, cholestatic cirrhosis, and cardiac cirrhosis, but is not limited thereto.

The term "liver fibrosis" as used herein refers to the process of wound healing by combining extracellular matrix (ECM) with mass-secreted collagen from active hepatic stellate cells as inflammatory reaction continuously progresses due to tissue damage. Such a continuous progression of liver fibrosis leads to liver cirrhosis having abnormal structures that the deposition of collagen occurs in liver tissue in large amount and regenerative nodules are surrounded by collagen.

The term "liver cirrhosis" as used herein is referred to as hepatic cirrhosis and refers to a chronic liver disease in which chronic inflammation causes normal hepatic tissue to turn into fibrotic tissue such as regenerative nodules (a phenomenon in which small lumps are formed) to lower liver function. It is a representative chronic liver disease, showing complex symptom by overlapping metabolic disturbances due to hepatic dysfunction and symptoms due to portal blood flow disorders. It may be divided into portal cirrhosis, necrotizing cirrhosis and biliary cirrhosis based in morphology and also divided into nutritional cirrhosis, alcoholic cirrhosis, viral hepatitis cirrhosis, cholestatic cirrhosis, and cardiac cirrhosis based on the cause.

Fibrosis of liver tissue can be progressed by various causes such as hepatitis virus, alcohol, and other toxic substances.

The exosomes or RNAs of the present invention have an effect of reducing the expression of α-SMA. Liver fibrosis is caused by chronic liver injury and is induced by a network of extracellular matrix and fibrosis-associated signaling system. Such a signaling system has a transforming growth factor β (TGF-β) signaling system. The composition of the present invention reduces the expression of α-SMA expressed in hepatic stellate cells activated by the TGF-β signaling system to inhibit liver fibrosis, and this has been specifically confirmed in Examples of the present invention.

The exosomes or RNAs of the present invention may further include one or more known active ingredients having an effect of preventing or treating liver fibrosis.

The pharmaceutical composition of the present invention may be formulated and administrated into a unit administrated form suitable for intra-body administration of an individual according to a conventional method in the pharmaceutical field. Suitable formulations for this purpose include injections such as injectable ampoules as parenteral administration formulations, injecting agents such as injection bags, and spray agents such as aerosol formulations. The injectable ampoule may be mixed with an injection solution immediately before use, and physiological saline, glucose, Ringer's solution, etc. may be used as an injection solution. The injection bag may be made of polyvinyl chloride or polyethylene.

The compositions of the present invention may further include suitable carriers commonly used in the manufacture of pharmaceutical compositions. For example, the injection solution further includes a preservative, a painless agent, a solubilizing agent, a stabilizer or the like, and the formulation for topical administration further includes a base, an excipient, a lubricant, a preservative or the like.

The compositions of the present invention may be administered to an individual in a variety of routes. All methods of administration may be expected, for example, by oral, rectal, intraperitoneal, intravenous, intramuscular, subcutaneous, intrauterine intradural or intra-cerebrovascular injection, preferably intraperitoneal, but is not limited thereto.

The exosomes, exosomal RNAs or composition of the present invention may be used alone or in combination with methods such as surgery, radiation therapy, hormone therapy, chemotherapy and method using biological response modifiers for the treatment or prevention of liver fibrosis.

The term "prevention" as used herein may refer to any action that inhibits or delays the onset of liver fibrosis by administering to individuals the composition for the prevention or treatment of liver fibrosis according to the present invention.

The term "treatment" may refer to any action that improves or ameliorates the symptoms of liver fibrosis by administering to individuals suspected of developing liver fibrosis the composition according to the present invention The term "individual" as used herein may refer to all animals, including humans, who have developed or are likely to develop liver fibrosis.

Further, the composition of the present invention may be added to a food composition, preferably a health functional food, for the purpose of preventing or improving liver fibrosis.

The term "health functional food" as used herein refers to a food having a biological control function such as prevention and improving of disease, biodefense, immunity, recovery after disease and anti-aging, when taken long-term, it should be harmless to the living body.

The mixed amount of the active ingredient included in the food composition of the present invention may be suitably determined according to the purpose of use (prevention, health or therapeutic procedure), but is not limited thereto.

Further, the present invention provides the cell therapeutic agent for preventing or treating liver fibrosis, in which the agent comprises an exosome or an exosomal RNA.

The term "cell therapeutic agent" as used herein refers to a therapeutic agent using autologous, allogenic, xenogenic cells for restoring the function of tissue, and means a cure used in the present invention for inhibiting liver fibrosis or cirrhosis.

The cell therapeutic agent of the present invention may be used as an agent for regenerating tissues selected from the group consisting of skin, cartilage, bone, blood vessel, brain, liver, heart, ligament, muscle, spinal cord, blood, bone marrow, lung, tooth, nerve, cornea, retina, esophagus, spine, kidney, pancreas or urethra, but is not limited thereto.

The present invention may include a vial, an ampule or a syringe in which the cell therapeutic agent is frozen and stored.

MODES OF THE INVENTION

Hereinafter, the present invention will be described in detail with reference to Examples and Preparation Examples. However, the following Examples and Preparation Examples are merely illustrative of the present invention, and the content of the present invention is not limited to the following Examples and Preparation Examples.

Example 1: Confirmation of Properties and Multipotentiality of Undifferentiated Mesenchymal Stem Cells Human umbilical cord-derived mesenchymal stem cells were purchased from ATCC (cat #ATCC-PCS-500-010). In order to examine property of the cells, the expressions of the markers of mesenchymal stem cells (CD44, CD73) and the non-marker factors (CD34, CD45) were confirmed by fluorescence activated cell sorting (FACS) analysis. The results are shown in FIG. 1.

As shown in FIG. 1, it was analyzed that the degree of the corresponding marker expression cells was 99.17% in the positive marker CD73 and 99.6% in CD44 compared with control. The negative markers CD34 and CD45 were expressed in 0.21% and 0.14%, respectively, indicating that there was little expression.

In addition, mesenchymal stem cells were induced to differentiate into osteocyte, chondrocyte, and adipocytes to confirm their differentiation potential. Stempro adipocyte differentiation kit, Stempro osteocyte differentiation kit, and Stempro chondrocyte differentiation kit (gibco), respectively, were used for differentiation into adipocytes, osteocyte and chondrocytes. For adipocyte and osteocyte differentiation, mesenchymal stem cells were seeded on a 12-well plate at $1\times10^4$ or $3\times10^4$ cells, respectively, and cultured for about 4 weeks while replacing the differentiation inducing culture medium by 3 days. After completion of differentiation, each cell was stained with Oil-red 0 and Alizarin-Red S to confirm whether or not they were differentiated. Chondrocyte differentiation was carried out by hanging-drop culture of $1\times10^4$ mesenchymal stem cells in 10 μl of culture medium for 48 hours, then transferring the formed cells with the spheroid to a cell culture plate, and culturing the cells for about 4 weeks while replacing the differentiation inducing culture medium by 3 days. The differentiated cells were frozen-sectioned to confirm whether or not they were differentiated by Alcian Blue staining. The results are shown in FIG. 2.

As shown in FIG. 2, it was verified that mesenchymal stem cells have multipotentiality.

Example 2: Confirmation of Proliferation of Mesenchymal Stem Cells in Culture Medium Containing Exosome Deficient FBS In order to secure undifferentiated mesenchymal stem cell- and hepatocyte-like cell-derived exosomes only, the exosomes should not be present in the FBS to be added to the basic culture medium of mesenchymal stem cells. Accordingly, the mesenchymal stem cell culture medium was supplemented with exosome deficient FBS, followed by the incubation. The WST assay was performed to confirm whether mesenchymal stem cells were proliferated.

Specifically, the measurement of the formation of the coloring substance called formazan in WST-1 (Tetrazolium Salts) caused by the mitochondrial dehydrogenase occurring in the cell metabolism indicates that it is effective only for living cells by succinatetrazolium reductase which is dehydrogenase, present in the mitochondrial electron transport system of metabolically active cells. Its color intensity shows a linear correlation with the number of cells. The results of the WST assay are shown in FIG. 3.

As shown in FIG. 3, it was confirmed that there was no difference in the proliferation of mesenchymal stem cells cultured in the basic culture medium supplemented with exosome-deficient FBS (Exo−) and mesenchymal stem cells cultured in the basic culture medium containing exosomes (Exo+). The mesenchymal stem cells cultured in the basic culture medium supplemented with exosome deficient FBS were thus used in the present invention.

Example 3: Cross-Differentiation Induction from Undifferentiated Mesenchymal Stem Cells to Hepatocyte-Like Cells In order to differentiate undifferentiated mesenchymal stem cells into hepatocyte-like cells, the differentiation was induced in a total of 4 steps by combining cytokines for the hepatocyte differentiation from undifferentiated mesenchymal stem cells as shown in FIG. 4.

As the first step, the cells were seeded at $3.0\times10^4$ cells/ $cm^2$ with a basic culture medium of mesenchymal stem cells on a cell culture plate coated with collagen type I at 5 ng/$cm^2$, and then the proliferation was induced at about 80% confluence. As the second step, the cells were cultured in Iscove's Modified Dulbecco's Medium (IMDM) containing epidermal growth factor (EGF) and basic fibroblast growth factor (bFGF) cytokines for 48 hours. As the third step to induce the differentiation, the cells were cultured in the culture medium supplemented with hepatocyte growth factor (HGH), basic FGF, nicotinamide and insulin-transferrin-sodium selenite (ITS) for 10 days while replacing the culture medium every two days. In the final maturation step, the hepatocyte-like cell differentiation was induced in IMDM supplemented with oncostatin M, dexamethasone, and ITS for more than 10 days while replacing the culture medium every two days. The results of inducing differentiation are shown in FIG. 5.

As shown in FIG. 5, morphological changes of the cells according to the differentiation induction steps were observed. As a result, it was confirmed that the cells were changed into polygonal cells in the final step (step 4).

Example 4: Confirmation of Properties of Mesenchymal Stem Cells and Differentiation Induced Hepatocyte-Like Cells In order to examine the change on hepatocyte-associated gene expression in hepatocyte-like cells in which the differentiation induction was completed, the expression of the gene expressed in the early hepatocyte in mesenchymal stem cells and hepatocyte-like cells at the mRNA level was comparative analyzed by conventional RT-PCR method. The results are shown in FIG. 6.

As shown in FIG. 6, it was confirmed that the expression was increased in all Sox17, AFT, albumin, TTR, TAT, CXCR4, G6pase, and Hnf4a, which play a major role in endodermal differentiation, hepatocyte maturation and hepatic metabolism. Further, it was confirmed that the expression of albumin in hepatocyte-like cells (HLCs) differentiation-induced by differentiation was significantly increased in mesenchymal stem cells (MSCs) thorough immunostaining.

In order to confirm the functional properties of hepatocytes in hepatocyte-like cells in which the induction of differentiation was completed, the following procedure was performed. Normal hepatocytes specifically have albumin and urea secretion, indocyanine green (ICG) absorption, and glycogen storage capacity. Accordingly, FIG. 7 shows the results of comparative analysis of the amount of albumin and urea secreted in the culture medium with mesenchymal stem cells by securing a cell culture medium induced to differentiate into hepatocyte-like cells.

As shown in FIG. 7, it was confirmed that the albumin and urea secretion were relatively high in hepatocyte-like cells (HLCs) statistically, and that albumin secretion was not significantly increased unlike the amount of gene expression.

In addition, periodic acid Schiff (PAS) staining was performed, and the results are shown in FIG. 8.

As shown in FIG. 8, it was confirmed that glycogen storage capacity was increased in hepatocyte-like cells, and the absorption was increased in hepatocyte-like cells when ICG was added to mesenchymal stem cells (MSCs) and hepatocyte-like cells (HLCs).

Therefore, it was confirmed that the hepatocyte-like cells derived as described above had characteristics represented by normal hepatocytes.

Example 5: Isolation and Property Analysis of Exosome in Mesenchymal Stem Cell and Hepatocyte-Like Cell Culture Media In order to separate the exosomes from the mesenchymal stem cells and hepatocyte-like cell culture media, the exosomes were obtained as shown in FIG. 9.

Specifically, mesenchymal stem cells or hepatocyte-like cells were cultured, and the culture medium was collected. Then, in order to separate the cells, the culture was centrifuged, and a 0.22 μm filter was used to remove the aggregate from the supernatant. In order to concentrate the culture medium containing exosomes, a 100-kDa cut-off centrifugal filter (ExoQuick-TC) 100 MWCO was used. Then the exosome extraction kit (ExoQuick-TC) was mixed with the culture medium. Then, the mixture was stored at low temperature for one day. Finally, the exosomes precipitated through centrifugation were extracted. The obtained exosomes were diluted with PBS, lysis buffer, or Trizol according to the following experiments.

The nanoparticle tracking assay (NTA) was performed using Nanosight equipment to confirm the size distribution of the exosomes obtained by isolating as described above. NTA is a method used to analyze exosomes and is an experimental technique that is visually identified by allowing nanoparticles to collect light scattered by a laser and to transmit the same to the equipment.

Specifically, the obtained exosomes were diluted with PBS in an appropriate concentration, they were placed in a Nanosight equipment, and the image of the exosomes reflected from the laser was analyzed to confirm the size distribution of the exosomes. The results are shown in FIG. 10.

As shown in FIG. 10, it was confirmed that the exosomes derived from mesenchymal stem cells (MSCs) and hepatocyte-like cells (HLCs) were present in a large amount at a size of 80 nm to 110 nm. These correspond to a representative size of exosomes known so far.

Thus, it was confirmed that the exosomes derived from mesenchymal stem cells and hepatocyte-like cells can be extracted by the above-mentioned method.

In addition, in order to confirm exosomes substantively, images were obtained using a transmission electron microscope (TEM). To prepare exosome samples for TEM, exosomes were fixed with paraformaldehyde (PFA) and attached to formvar-carbon EM grid. The grid was then post-fixed with glutaraldehyde and stored in uranyl oxalate for comparison and staining. Finally, embedding was carried out using methylcellulose-uranyl acetate solution. The results of observing the exosome through an electron microscope are shown in FIG. 11.

As shown in FIG. 11, mesenchymal stem cell (MSC) and hepatocyte-like cell (HLC) derived exosomes about 50-110 nm in size were confirmed through an electron microscope.

Example 6: Recovery Effect of Liver Injury by Exosome Administration to a Chronic Liver Fibrosis Animal Model 6-1. Production and Confirmation of Chronic Liver Fibrosis Animal Models A chronic liver fibrosis model was constructed by long-term administration of thioacetamide (TAA) to the peritoneal cavity of mice through a known method (3 times a week for 8 weeks). The hepatotoxicity test (ALT/AST) and Sirius Red staining were carried out in the serum of the mice in which TAA administration was completed. Then, it was confirmed whether a chronic liver fibrosis mouse model was produced. The results are shown in FIGS. 12 and 13.

As shown in FIG. 12, the hepatic toxicity test results indicated that both serum AST and ALT values were high in the TAA-administered mouse experimental group (TAA). In addition, as shown in FIG. 13, the Sirius red staining results indicated that the degree of deposition of collagen was high in TAA-administered mouse group (TAA).

Therefore, the animal model produced by this method was utilized as a study resource for chronic liver fibrosis animal models for the treatment of mesenchymal stem cell and hepatocyte-like cell exosomes.

6-2. Confirmation of Change on Hepatotoxicity by Administration of Exosomes

In order to obtain a mouse model for confirmation of liver recovery by exosome administration, TAA was administered for a prolonged period of time using the verified method to produce chronic liver fibrosis mouse models (total of 20 mice including 5 mice without administration, 5 mice administered with TAA and then saline, 5 mice administered with TAA and then MSC exosomes and 5 mice administered with TAA and then HLC exosomes).

The number of purified exosomes in mesenchymal stem cells and hepatocyte-like cells was quantified by NTA. Then, approximately $3 \times 10^9$ exosomes were injected directly into the abdominal cavity of the chronic liver fibrosis animal model. At the same time, the same amount of saline was administered therewith, and they were used as a control group for liver damage recovery efficacies.

Three days after the administration of exosomes, hepatoxicity test (ALT/AST) was performed in the serum of the control group (without administration, normal; administrated with saline: sham) and the experimental group (MSC-exo, HLC-exo). Then, the recovery efficacy for liver damage was confirmed, and the results are shown in FIG. 14.

As shown in FIG. 14, it was confirmed that the AST and ALT values of MSC-exo and HLC-exo were significantly decreased compared with those of sham. This suggests that exosomes derived from mesenchymal stem cells and hepatocyte-like cells indirectly have therapeutic efficacy for liver damage.

6-3. Analysis of Collagen Deposition by Administration of Exosome

Liver fibrosis is the process of wound healing by combining extracellular matrix (ECM) with mass-secreted collagen in active hepatic stellate cells as the inflammatory reaction continuously progresses due to liver tissue damage. Such a continuous progression of liver fibrosis leads to liver cirrhosis having abnormal structures that the deposition of collagen occurs in liver tissue in large amount and regenerative nodules are surrounded by collagen. It is therefore essential to identify the collagen deposited by the liver damage healing response.

In order to analyze the collagen deposition according to the administration of exosomes, 3 days after the exosome administration in the control group as described above, hepatic tissues were separated from the mice to prepare paraffin blocks. Sirius red staining was then performed using the sections, and the degree of collagen deposition was quantitatively comparative analyzed with the control group. The results are shown in FIG. 15.

As shown in FIG. 15, it was confirmed that the degree of collagen deposition in MSC-exo and HLC-exo was significantly decreased compared with those of sham as in the result of the hepatotoxicity test.

6-4. Analysis of Hepatic Stellate Cells and Kupffer Cell Activities by Exosome Administration It is important to identify hepatic stellate cells and Kupffer cells activities to examine the degree of liver damage. The hepatic stellate cells play an important role in the formation of collagen and extracellular matrix, and Kupffer cells act as macrophages to remove bacteria and toxins when they enter, and release various cytokines and reactive oxygen species (ROS) when activated. These affect hepatocyte, endothelial cell, and hepatic stellate cell to promote liver fibrosis.

In order to confirm the activity of hepatic stellate cells and Kupffer cells, after 3 days of treatment with exosomes, hepatic tissues were isolated from the mice, and paraffin blocks were prepared. The sections were stained with alpha-smooth muscle actin ($\alpha$-SMA) and F4/80, respectively, to confirm the activity of hepatic stellate cells and Kupffer cells. The results are shown in FIG. 16.

As shown in FIG. 16, the activity of hepatic stellate cells and Kupffer cells in MSC-exo and HLC-exo was decreased compared with those of sham.

Example 7: Confirmation of Therapeutic Efficacy of Exosomes on Liver Fibrosis Due to Decrease in $\alpha$-SMA Expression in Hepatic Stellate Cells Liver fibrosis is caused by chronic liver damage, which is induced by a complex network of extracellular matrix and fibrosis-related signaling system. In order to examine whether it is associated with the transforming growth factor $\beta$ (TGF-$\beta$) signaling system, the liver fibrosis-recovery efficacy was verified by comparing and analyzing the amount of $\alpha$-SMA expression after treatment with exosomes in active hepatic stellate cells.

Specifically, the hepatic stellate cells in culture were seeded on a 6-well plate at $5 \times 10^4$ cells/cm$^2$, and after 24 hours, the culture medium was replaced with a culture medium containing 0.2% FBS to produce a quiescent hepatic stellate cell. Then, the cells were treated with 10 ng/ml human TGF-$\beta$ for 24 hours to culture the cells in an active state by TGF-$\beta$. While the cells were treated with TGF-$\beta$, the cells were treated with about $3 \times 10^9$ exosomes. Thus, the activation of the TGF-$\beta$ signaling system was confirmed through the amount of SMAD2 protein expression. The expression level of $\alpha$-SMA was comparative-analyzed with that of the control group. Thus, the results of verifying therapeutic efficacy on liver fibrosis are shown in FIG. 17.

As shown in FIG. 17, the $\alpha$-SMA expression was decreased in serum-free (SF) medium treatment and increased again in TGF-$\beta$ treatment. Further, it was confirmed that the $\alpha$-SMA expression was decreased when treated with mesenchymal stem cells and hepatocyte-like cell exosomes at the same time.

Thus, it was confirmed that the mesenchymal stem cells and hepatocyte-like cell exosomes were effective in the treatment of liver fibrosis.

Example 8: Isolation and Confirmation of Exosomal Small RNA

In order to isolate small RNAs present in exosomes derived from mesenchymal stem cells and hepatocyte-like cells that are effective in the treatment of liver fibrosis as described above, the conventional Trizol (phenol-guanidine thioacetamide) method was modified and carried out.

Specifically, 700 µl of Trizol was mixed to the exosome precipitate, and 140 µl of chloroform was mixed thereto, followed by performing vortex. The result was centrifuged at 15,000×G at 4° C. for 15 minutes to separate the liquid phase and the organic phase. Then, the isolated liquid phase was mixed with 500 µl of 70% (v/v) ethanol to precipitate RNA having about 200 nt or more. The centrifugation was performed at 15,000×G at 4° C. for 15 minutes to separate the precipitate. The supernatant was placed and mixed with 500 µl of 100% ethanol and 1 µl of 10 mg/ml glycogen, and the mixture was stored at room temperature for 30 minutes to precipitate RNA having about 200 nt or less. Then, the precipitate was separated by centrifugation at 15,000×G at 4° C. for 15 minutes, the supernatant was removed, and then 700 µl of 70% ethanol was added thereto. Then, washing was carried out. Finally, the precipitate was separated by centrifugation at 15,000×G at 4° C. for 5 minutes to isolate the precipitate. The isolated RNAs were dissolved with 15 µl of nuclease-free water. Then, RNAs were mixed in 2× gel loading buffer, and then separated according to size in 12% polyacrylamide gel. The result was stored in toluidine blue stain (TBO) solution (0.016% TBO, 2% methanol, 0.04% acetate) at room temperature for 20 minutes to stain RNAs.

The deionized distilled water was changed every 10 minutes to remove stain on the gel. The results are shown in FIG. 18.

As shown in FIG. 18, it was confirmed that RNAs having 200 nt or less or 200 nt or more were well isolated, and the efficacy of treating liver fibrosis was examined at the cell level using small RNAs having 200 nt or less in the following.

Example 9: Identification and Analysis of Exosomal Small RNA by High-Throughput Sequencing Based on the results of Example 8, the following experiment was carried out to identify exosomal small RNA. First, the exosomes derived from HeLa and HEK293T cells were obtained. They were administrated to liver damage animal models. Then, it was confirmed that the numbers of macrophages (F4/80) and active hepatic stellate cells (α-SMA) were not significantly different from those of the control group. In comparison with liver fibrosis-associated gene expression patterns, the live tissue treated with HeLa cell-derived exosomes showed the most similar expression patterns to those of the control group and were selected as control exosomes of high-throughput sequencing (see FIG. 19). The results of high-throughput sequencing are shown in FIG. 20.

As shown in FIG. 20, 1,247 out of 2,588 human microRNAs reported so far were identified for exosomal microRNAs. 929, 681, and 836 mircoRNAs were identified in the control exosome and exosomes derived from mesenchymal stem cells, and hepatocyte-like cells, respectively. Further, the additional analyzes showed that there were 78 microRNAs in the mesenchymal stem cell exosomes and 69 microRNAs in the differentiated hepatocyte-like cell exosomes compared to the control exosomes. It was confirmed that of these, 57 microRNAs were commonly significantly included in exosomes derived from two cells with anti-liver fibrosis efficacy in a large amount. Thus, the 57 microRNAs were first selected.

Example 10: Selection and Production of Anti-Liver Fibrosis Candidate RNA

Based on the results of analysis of the liver fibrosis-related network and exosomal RNA sequencing, a total of 5 microRNAs expected to have anti-liver fibrosis efficacy were secondly selected among the microRNAs first selected in Example 9. The sequences are shown in Table 1 and custom made to a private biotechnology company, and thus the sequence was obtained.

TABLE 1

| No | miRNAs | Orientation | Sequence (5' to 3') |
|---|---|---|---|
| 1 | Control miRNA | Sense | UUCUCCGAACGUGUCACGUTT |
|  |  | Antisense | ACGUGACACGUUCGGAGAATT |
| 2 | hsa-miR-136 | Sense | CAUCAUCGUCUCAAAUGAGUCU (SEQ. ID NO: 1) |
|  |  | Antisense | ACUCCAUUUGUUUUGAUGAUGGA |
| 3 | hsa-miR-199a | Sense | ACAGUAGUCUGCACAUUGGUUA (SEQ. ID NO: 2) |
|  |  | Antisense | CCCAGUGUUCAGACUACCUGUUC |
| 4 | hsa-miR-409 | Sense | GAAUGUUGCUCGGUGAACCCU (SEQ. ID NO: 3) |
|  |  | Antisense | AGGUUACCCGAGCAACUUUGCAU |

TABLE 1 -continued

| No | miRNAs | Orientation | Sequence (5' to 3') |
|---|---|---|---|
| 5 | hsa-miR-410 | Sense | AGGUUGUCUGUGAUGAGUUCG (SEQ. ID NO: 4) |
|  |  | Antisense | AAUAUAACACAGAUGGCCUGU |
| 6 | hsa-miR-432 | Sense | UCUUGGAGUAGGUCAUUGGGUGG (SEQ. ID NO: 5) |
|  |  | Antisense | CUGGAUGGCUCCUCCAUGUCU |

5 kinds of second-selected microRNAs were transfected into active hepatic stellate cells, and the activity of hepatic stellate cells was confirmed by Western blot analysis. The results are shown in FIG. 21.

As shown in FIG. 21, it was confirmed that the 5 kinds of second-selected microRNAs had the effect of reducing the hepatic stellate cell activity.

Example 11: Verification of Efficacy of Anti-Liver Fibrosis microRNAs in Chronic Liver Fibrosis Animal Models In order to confirm the anti-liver fibrosis efficacy of microRNA, experiments were performed using an animal model of chronic liver fibrosis. However, it has been expected that direct injection of microRNA into the abdominal cavity of mice will not be efficiently transferred to liver tissue due to degradation by various RNA degrading enzymes present in the living body. Therefore, each of the selected microRNAs was injected into exosomes which can be stably transferred into specific tissues and cells in vivo. They were administrated into abdominal cavity of mice to stably transfer microRNAs into the liver tissue. First, in order to fuse a peptide capable of targeting hepatic stellate cells to membrane protein (Lamp2b) of exosome, plasmid DNAs were prepared, and transfected on HeLa cells and HEK293T cells. Then, the exosomes of each cell were extracted using an exosome extraction kit (Exoquick-TC) through the method described in Example 5. In order to confirm the effective delivery of microRNAs to hepatic stellate cells using these, 100 pmole RNAs with red fluorescent substance attached to each $3 \times 10^9$ exosomes were injected into exosome using Exofect reagent. Then, the result was added to the active hepatic stellate cell culture medium. The results are shown in FIG. 22.

As shown in FIG. 22, it was confirmed that when exosomes injected with RNAs were added to the hepatic stellate cell culture medium, the RNAs were introduced into the hepatic stellate cells twice or more in the case in which the HeLa cell-derived exosomes were utilized.

Next, liver fibrosis animal models were prepared by repeatedly administering thioacetamide (TAA), a hepatotoxic substance, to the abdominal cavity of mice for 8 weeks (3 times per week). Then, through the method established above, $3 \times 10^9$ exosomes injected with 100 pmoles of microRNAs (miR-409 or miR-410) were administered to the abdominal cavity of mice. 3 days later, the mice were sacrificed, liver tissues were separated, and Sirius red staining and immunofluorescence staining were performed according to a conventionally known method. The results are shown in FIGS. 23 and 24.

As shown in FIG. 23, it was confirmed by Sirius Red staining that collagen deposition in liver tissue was inhibited by administration of miR-409 and miR-410.

In addition, as shown in FIG. 24, it was confirmed by immunofluorescence staining that the number of macrophages (F4/80) and active hepatic stellate cells (α-SMA), a major cause of liver fibrosis was decreased by administration of miR-409 and miR-410.

From the above results, it was confirmed that the exosome of the present invention and the RNAs derived therefrom have effects of inhibiting the activity of hepatic stellate cells and Kupffer cells and decreasing the expression of α-SMA and an excellent effect of inhibiting the deposition of collagen to suppress the progress of liver fibrosis.

Although the present invention has been described with reference to the preferred embodiments mentioned above, it is possible to make various modifications and variations without departing from the spirit and scope of the invention. Further, the appended claims include such modifications and variations as fall within the scope of the present invention.

The invention claimed is:

1. A method for treating liver fibrosis, the method comprising administering an exosomal RNA to an individual in need thereof,
   wherein the exosomal RNA is a microRNA selected from the group consisting of miR-136, miR-199a, miR-409, miR-410 and mir-432.

2. The method of claim 1, wherein the exosome is derived from a mesenchymal stem cell or a hepatocyte-like cell,
   wherein the hepatocyte-like cell has increased expression levels of Sox17, AFT, albumin, TTR, TAT, CXCR4, G6pase, and Hnf4a,
   wherein the hepatocyte-like cell has increased levels of albumin and urea secretion, and
   wherein the hepatocyte-like cell has increased glycogen storage capacity.

3. The method of claim 1, wherein the miR-136 consists of the nucleotide sequence represented by SEQ ID NO: 1.

4. The method of claim 1, wherein the miR-199a consists of the nucleotide sequence represented by SEQ ID NO: 2.

5. The method of claim 1, wherein the miR-409 consists of the nucleotide sequence represented by SEQ ID NO: 3.

6. The method of claim 1, wherein the miR-410 consists of the nucleotide sequence represented by SEQ ID NO: 4.

7. The method of claim 1, wherein the miR-432 consists of the nucleotide sequence represented by SEQ ID NO: 5.

8. The method of claim 1, wherein the liver fibrosis is at least one selected from the group consisting of liver fibrosis, portal cirrhosis, necrotizing cirrhosis, biliary cirrhosis, nutritional cirrhosis, alcoholic cirrhosis, viral hepatitis cirrhosis, cholestatic cirrhosis, and cardiac cirrhosis.

9. A method for improving liver fibrosis, the method comprising administering a food composition comprising an exosomal RNA,
   wherein the exosomal RNA is a microRNA selected from the group consisting of miR-136, miR-199a, miR-409, miR-410 and mir-432.

10. A method for treating liver fibrosis, the method comprising administering a cell therapy agent comprising an exosomal RNA,
    wherein the exosomal RNA is a microRNA selected from the group consisting of miR-136, miR-199a, miR-409, miR-410 and mir-432.

* * * * *